United States Patent
Suh et al.

(10) Patent No.: US 6,800,247 B1
(45) Date of Patent: Oct. 5, 2004

(54) DEACTIVANTS FOR DUST MITE ALLERGENS

(75) Inventors: Janette Suh, Ho-Ho-Kus, NJ (US); Gay Cornelius, Cottingham (GB); Malcolm Tom McKechnie, Driffield (GB); Ian Andrew Thompson, New South Wales (AU)

(73) Assignee: Reckitt Benckiser (UK) Limited, Slough (GB)

( * ) Notice: Subject to any disclaimer, the term of this patent is extended or adjusted under 35 U.S.C. 154(b) by 0 days.

(21) Appl. No.: 09/509,308
(22) PCT Filed: Sep. 22, 1998
(86) PCT No.: PCT/GB98/02863
  § 371 (c)(1),
  (2), (4) Date: May 25, 2000
(87) PCT Pub. No.: WO99/15208
  PCT Pub. Date: Apr. 1, 1999

(30) Foreign Application Priority Data

Sep. 25, 1997 (GB) ............................................... 9720275
Sep. 25, 1997 (GB) ............................................... 9720298

(51) Int. Cl.[7] ........................ A01N 25/00; A01N 59/16; A01N 65/00
(52) U.S. Cl. ........................ 422/28; 424/405; 424/618; 424/725; 424/770
(58) Field of Search ........................ 422/5, 4, 28, 32; 424/405, 43, 126, 600, 618, 725, 770

(56) References Cited

U.S. PATENT DOCUMENTS

| | | | |
|---|---|---|---|
| 3,777,016 A | 12/1973 | Gilbert | 424/80 |
| 4,073,954 A | 2/1978 | Mobius | 426/330.3 |
| 4,715,387 A | 12/1987 | Rose | 131/270 |
| 4,752,466 A | 6/1988 | Saferstein et al. | 424/46 |
| 4,806,526 A | 2/1989 | Green | 514/23 |
| 5,320,872 A | 6/1994 | McNeel et al. | 427/393 |
| 5,415,815 A | 5/1995 | Bruno | 252/582 |
| 5,461,751 A | 10/1995 | Sepke | 15/246.3 |
| 5,635,132 A | 6/1997 | Blanc | 422/5 |
| 5,965,602 A | * 10/1999 | Takada et al. | 514/428 |

FOREIGN PATENT DOCUMENTS

| | | | |
|---|---|---|---|
| EP | 0 716 143 A1 | 6/1996 | ............ C11D/3/00 |
| GB | 1167173 | 10/1969 | ............ C09K/3/30 |
| GB | 1397216 | 6/1975 | ............ C11D/10/06 |
| GB | 2300122 A | 10/1996 | |
| WO | WO96/04937 | 2/1996 | ............ A61L/9/01 |
| WO | 96/09762 A1 | 4/1996 | |
| WO | WO-99/53763 A1 | * 10/1999 | |

OTHER PUBLICATIONS

Woodfolk et al. "Chemical treatment of carpets to reduce allergen: A detailed study of the effects of tannic acid on indoor allergens," J. of Allergy and Clinical Immunology (1994), 94(1), pp. 19–26.*

Green, W. F. "Abolition of allergens by tannic acid," Lancet (1984), 2(8395), p. 160.*

JP 06 237979 A Abstract.

(List continued on next page.)

*Primary Examiner*—Elizabeth McKane
(74) *Attorney, Agent, or Firm*—Fish & Richardson P.C.

(57) ABSTRACT

Der-f and/or Der-p dust mite allergens are deactivated by an amount of one or more of the following deactivants: i) cedarwood oil, ii) hexadecyltrimethylammonium chloride, iii) aluminium chlorohydrate, iv) 1-propoxy-propanol-2, v) polyquaternium-10 vi) silica gel, vii) propylene glycol alginate, viii) ammonium sulphate, ix) hinokitiol, x) L-ascorbic acid, xi) immobilised tannic acid, xii) chlorohexidine, xiii) maleic anhydride, xiv) hinoki oil, xv) a composite of AgCl and $TiO_2$, xvi) diazolidinyl urea, xvii) 6-isopropyl-m-cresol, xviii) a compound of formula I

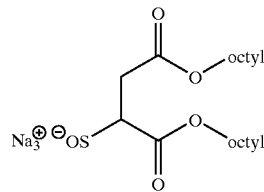

xix) the compound of formula II

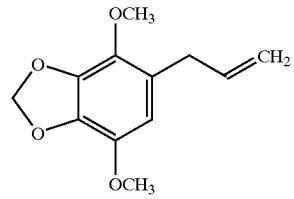

xx) a polymeric dialdehyde containing two or more of a recurring unit of the formula III

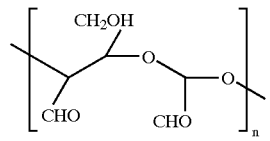

where n=2 to 200, xxi) urea, xxii) cyclodextrin, xxiii) hydrogenated hop oil, xxiv) polyvinylpyrrolidone, xxv) N-methylpyrrolidone, xxvi) the sodium salt of anthraquinone, xxvii) potassium thioglycolate, and xxviii) glutaraldehyde. Deactivants (i) to (xx) are effective against allergens derived from both species. Deactivants (xxi) to (xxvi) are effective against only Der-f allergens. Deactivants (xxvii) and (xxviii) are effective against only Der-p allergens. Aerosol compositions comprise said deactivants, a propellant and optional solvents.

11 Claims, No Drawings

OTHER PUBLICATIONS

JP 04 013607 A Abstract.
JP 08 113509 A Abstract.
JP 01 242508 A Abstract.
JP 08 103402 A Abstract.

JP 55-069682 A Abstract.

Chem. Abstract 69:75913—Honma, "Effect of Various Chemicals on Mites".

* cited by examiner

DEACTIVANTS FOR DUST MITE ALLERGENS

BACKGROUND OF THE INVENTION

It has been known for a long time that house dust can trigger allergenic reactions in humans, such as asthma and rhinitis. It was reported, as early as 1928, that it was the dust mites in the dust that were the primary source of the allergenic response but it was only in the 1960's that researchers appreciated its significance.

It is believed that the faeces of two particular house dust mite species, *Dermatophagoides farinae* (known as Der-f) and *Dermatophagoides pteronyssinus* (known as Der-p) trigger the immune responses of the body, thereby giving rise to well known allergenic symptoms.

A review of this is given in Experimental and Applied Acarology, 10 (1991) p. 167–186 in an article entitled "House dust-mite allergen": A review by L. G. Arlian.

Both the Der-f and Der-p species are found throughout the world. In some areas, Der-f will be the sole Dermatophagoides species. In other areas Der-p will be the sole species. In still other areas, the two species are both present through, generally, one or the other will predominate.

One way to overcome these allergenic response has been to vacuum surfaces, such as carpets, that contain the dust mites and their faeces thoroughly and often, but that is both time consuming (i.e. has to be regularly done if one wants to make an allergenic free environment) and is very dependent on the efficiency of vacuum cleaner and filter bag used e.g. micron filter bag or 2-layer vacuum bags.

An alternative method of creating an allergen-free environment has been to denature the allergen, for example as described in U.S. Pat. No. 4,806,526. The only effective method however of which we are aware is to apply tannic acid to the allergen. However, tannic acid can cause staining, and this is a particularly acute problem for light coloured carpets (e.g. white and light beige carpets) and other textile surfaces as tannic acid leaves a deep brown stain.

Therefore, we have been looking for allergenic dehaturants which will not stain susceptible surfaces such as carpets and still deactivate the allergen.

We have discovered a number of allergen deactivants which are effective against both the Der-f and the Der-p species. Quite surprisingly, we have discovered that some of these deactivants are specific to the type of dust mite allergen being treated. For example an effective Der-f allergen deactivants will not automatically work effectively as a Der-p allergen deactivant.

DISCLOSURE OF THE INVENTION

According to the invention there is provided a method for deactivating allergens derived from the Der-f and/or Der-p dust mite species, which comprises contacting the allergen with a deactivating effective amount of one or more of deactivants (herein after defined as the deactivant).

The deactivants effective against one or both of Der-f allergens and Der-p allergens are:
i) cedarwood oil,
ii) hexadecyltrimethylammonium chloride,
iii) aluminium chlorohydrate,
iv) 1-propoxy-propanol-2,
v) polyquaternium-10
vi) silica gel,
vii) propylene glycol alginate,
viii) ammonium sulphate,
ix) hinokitiol,
x) L-ascorbic acid,
xi) "immobilised tannic acid", (hereinafter defined)
xii) chlorohexidine,
xiii) maleic anhydride,
xiv) hinoki oil,
xv) a composite of AgCl and $TiO_2$,
xvi) diazolidinyl urea,
xvii) 6-isopropyl-m-cresol,
xviii) a compound of formula I

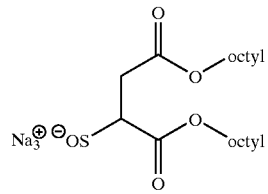

xix) the compound of formula II

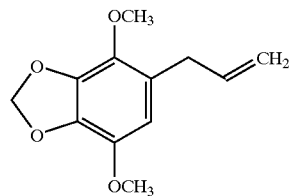

xx) a polymeric dialdehyde containing two or more of a recurring unit of the formula III

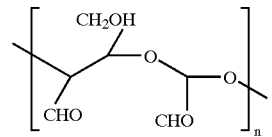

where n=2 to 200,
xxi) urea,
xxii) cyclodextrin,
xxiii) hydrogenated hop oil,
xxiv) polyvinylpyrrolidone,
xxv) N-methylpyrrolidone,
xxvi) the sodium salt of anthraquinone,
xxvii) potassium thioglycolate, and
xxviii) qlutaraldehyde Deactivants (i) through (xx) are effective against both Der-f and Der-p allergens. Deactivants (xxi) through (xxvi) are effective against Der-f allergens only. Deactivants (xxvii) and (xxviii) are effective against Der-p allergens only.

A compound of formula I is commercially available as Aerosol OT.

The compound of formula II is commercially available as parsley camphor.

Hinoki oil is a mixture of thujan-3-one, 2-pinene, 3,5,7,3',4'-pentahydroflavanone and 1,3,3-trimethyl-2-norcamphanone.

Hydrogenated Hop Oil is the potassium salt of tetrahydroiso humulinic acid. (also known as reduced isomerised hop extract).

Propylene glycol alginate is

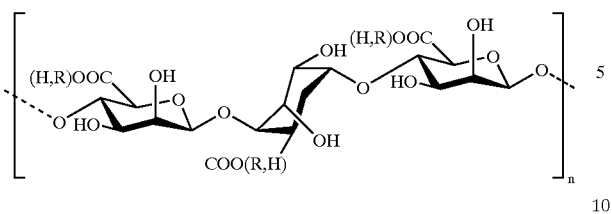

Chlorohexadine is 1,1'-hexamethylenebis [5-(4-chlorophenyl)]-biguanide.

Hinokitol is β-thujaplicin, a compound of the formula

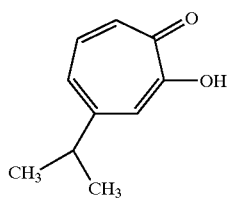

Germall II is diazolidinylurea.

Thymnol is 6-isopropyl-m-cresol.

Cedarwood oil contains α- and β-cedrene (ca 80%), cedrol (3–14%) and cedrenol. Other sesquiterpenes and some monoterpenes are also present.

Polyquaternium-10 is a polymeric quaternary ammonium salt of hydroxyethyl cellulose reacted with a trimethyl ammonium substituted epoxide commercially available as Polymer JR-125.

Silica gel is also known as colloidal silica or silicic acid and is commercially available as Kent.

"Immobilised tannic acid" is tannic acid on polyvinyl pyrrolidone beads. Immobilised Tannic Acid was prepared as follows: 100 mg of tannic acid was dissolved in water; 50 mg of Polyclar 10 (ISP, Guildford Surrey) polyvinyl pyrrolidone beads were added and stirred for one hour; the beads were filtered off the solution and washed with a few mls of iced water until no colour was seen in the washings; they were then dried in the oven at 50° C.

The composite of silver chloride and $TiO_2$ is made up of 20% wt/wt AgCl on 80% $TiO_2$ 3–5 μm porous beads.

In compositions containing the deactivant, the deactivant is present in an amount of from 0.01% to 7%, preferably from 0.01% to 3%.

In methods for treating rugs and carpets to deactivate allergents, the amount of deactivant present is from about 16 gm to about 170 gm per 10 square meters, preferably about 32 gm per 10 square meters.

Preferably the deactivant is selected from
xiv) hinoki oil,
xv) a composite of AgCl and $TiO_2$,
xvi) diazolidinyl urea
xvii) 6-isopropyl-m-cresol,
xii) chlorohexidine,
xiii) maleic anhydride,
xxvi) the sodium salt of anthraquinone and
xviii) a compound of formula I or II, defined above, and
xix) a compound of formula II, defined above.

Further according to the invention there is provided an aerosol composition containing
i) cedarwood oil,
ii) hexadecyltrimethylammonium chloride,
iii) aluminium chlorohydrate,
iv) 1-propoxy-propanol-2,
v) polyquaternium-10
vi) silica gel,
vii) propylene glycol alginate,
viii) ammonium sulphate,
ix) hinokitiol,
x) L-ascorbic acid,
xi) "immobilised tannic acid", (hereinafter defined)
xii) chlorohexidine,
xiii) maleic anhydride,
xiv) hinoki oil,
xv) a composite of AgCl and $TiO_2$,
xvi) diazolidinyl urea,
xvii) 6-isopropyl-m-cresol,
xviii) a compound of formula I

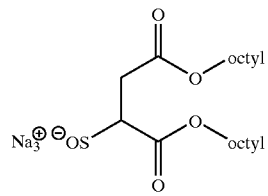

xix) the compound of formula II

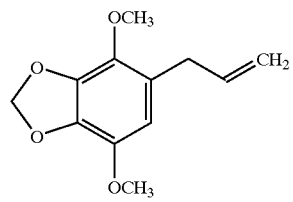

xx) a polymeric dialdehyde containing two or more of a recurring unit of the formula III

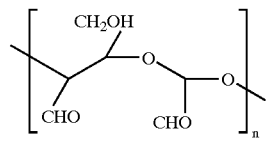

where n=2 to 200,
xxi) urea,
xxii) cyclodextrin,
xxiii) hydrogenated hop oil,
xxiv) polyvinylpyrrolidone,
xxv) N-methylpyrrolidone,
xxvi) the sodium salt of anthraquinone,
xxvii) potassium thioglycolate, and
xxviii) qlutaraldehyde
b) a propellant, and
c) optionally, a solvent.
b) a propellant, and
c) optionally, a solvent.

Preferably the amount of deactivant present in such a composition is from 0.01% to 7%, more preferably 0.01% to 3%, Preferably the amount of propellant present in such a composition is from 4% to 50%, more preferably from 4% to 30%, Preferably the amount of solvent present in such a composition is 0% to 99.95%, more preferably 0% to 90%, and most preferably from 20% to 90%.

Preferably the deactivant in such aerosol composition is selected from hinoki oil, a composite of AgCl with $TiO_2$, diazolidinyl urea, 6-isopropyl-m-cresol, chlorohexidine, maleic anhydride, the sodium salt of anthraquinone, and a compound of formula I or II defined above.

Preferably the propellant is selected from those commercially available, for example $C_{1-4}$ alkanes, chlorofluorocarbons and compressed gases such as nitrogen, air and carbon dioxide.

Preferably the solvent is selected from $C_{1-6}$ alcohols (e.g. ethanol) or water.

In addition, the compositions of this invention may also contain one or more of the following:

- a fragrance, preferably in an amount of 0% to 5%, more preferably 0% to 2%;
- an antimicrobial compound e.g. alkyldimethylbenzyl ammonium saccharinate, preferably in an amount of 0.01% to 1%;
- a surfactant, e.g. Dow Corning 193 Surfactant, preferably in an amount of 0.01% to 10%;
- a corrosion inhibitor, e.g. sodium nitrite, sodium benzoate, triethanolamine and ammonium hydroxide, preferably in an amount of 0.01% to 10%; and
- a miticide, such as benzyl benzoate, pyrethroid pemethrin, d-allethrin and optionally a synergist such as piperonyl butoxide, preferably in an amount of 0.1% to 10%.

It has been found that deactivants of the invention have as effective allergen deactivating properties as tannic acid but without the drawback of staining.

The invention will now be illustrated by the following Examples.

EXAMPLES

The test procedure in Examples 1 to 55 is as follows and is known as the ELISA protocol.

The ELISA protocol for Der-f and Der-p has been developed as follows as a measure of denaturing property for denaturants.

ELISA Protocol 1

1. Dust is collected from Hoover™ vacuum cleaner bags and passed through a series of sieves down to 63 microns.
2. Clean petri dishes are labelled with the chemical to be tested (on the base). Three replicates are used for each treatment.
3. Filter paper is used to line each dish and 0.2 g of dust is added to each dish onto the filter paper. The lid (or base, as dishes are inverted) is replaced and the dish is shaken to disperse the dust evenly over the filter paper.
4. 2% aqueous solutions of deactivant were used except for the silver chloride composite where 0.05% was used instead. Immobilised tannic acid was used as a 1% dispersion. The hydrogenerated hop end was used at the 2% level (in the form of a 10% solution). Water-insoluble deactivants were emulsified with a sorbitone oleate surfactant (i.e. Tween). Hinokitol was used at 0.5% not 2%.
5. The dust is sprayed with the corresponding treatment, 2 sprays are required for sufficient coverage (1 spray=1.5 ml).
6. Leave uncovered at room temperature, in well aerated room, until filter paper is dry. This can take up to 4 hours.
7. Empty dust in epindorfs labelled according to treatment.
8. Add 1 ml of 5% Bovine Serum Albumen Phosphate Butter Saline—Tween BSA-PBS-T to each epindorf (5 times the weight of dust) (20 ml of BSA-PBS-T=1 g of BSA in 20 ml of PBS-T).
9. Leave overnight in a refrigerator.
10. Centrifuge for 5 minutes at 13,000 rpm.
11. Decant the supernatant into a new epindorf labelled according to treatment.
12. Centrifuge again for 5 minutes at 13,000 rpm.
13. Make up dilutions of 1:10 and 1:100 by adding 100 µl of neat solution to 900 µl of 1% BSA-PBS-T (1:10). This is repeated using 100 µl of 1:10 dilution and add to 900 µl of 1% BSA-PBS-T for 1:100 dilution.

ELISA Protocol 2 for Der-f and Der-p: Indoor Biotechnologies

1. Prepare samples and dilutions as in protocol
2. Prepare 500 ml of 50 mM carbonate/bicarbonate buffer by dissolving 0.795 g $Na_2CO_3$ and 1.465 g $NaHCO_3$ in 500 ml of distilled water. Check the pH is at 9.6. (This solution is kept in the refrigerator in a conical flask).
3. Monoclonal antibody (kept in the freezer) has to be added to the buffer using the following method, (1 µg per well; 11 ml is needed) applied to the ELISA plate
   11 ml of carbonate/bicarbonate buffer is added to the dispensing tray.
   11 µl of Der-f1 or Der-p1 monoclonal antibody
   (Stored in freezer, epindorf in use is in the refrigerator) is added to the buffer. To ensure that all the antibody is removed from the tip, wash out the pipette tip by sucking up and down I the buffer solution, gently stirring to mix thoroughly.
4. Pipette 100 µl of the antibody solution into each well of the microtiter plate, cover with a plate sealer and leave overnight at 4° C.
5. Empty the plate by quickly inverting it over the sink, then dry by banging on a stack of paper towels.
6. Add 200 µl of wash buffer to each well: PBS/0/05% tween (PBS-T)
7. Repeat stages 5 and 6 once more (making a total of 2 washes).
8. Make sure all the wells are dry, then add 100 µl of 1% BSA-PBS-T. Replace the plate sealer and incubate for 1 hour at room temperature*.
9. Repeat steps 5 to 7 (2 washes).
10. *During the hour incubation period, prepare the allergen standards at dilutions between 125 and 1 µg/ml Der f 1 or Der p1:
    Add 25 µl of allergen standard (kept in the refrigerator in polystyrene box) to 475 µl of 1% PBS-BSA-T and mix thoroughly—labelled '125'.
    250 µl of 1% PBS-BSA-T is added to 7 further epindorfs which are labelled 62.5, 31.25, 15.63, 7.61, 3.9, 1.95 and 0.98.

250 µl is taken from the 1st epindorf (labelled 125) and transferred to the next (labelled 62.5). This is mixed thoroughly.

Using a new pipette tip, 250 µl is removed from epindorf labelled 62.5 and transferred to 31.25, this procedure is continued down to the 0.98 concentration (125, 62.5, 31.25, 15.63, 7.61, 3.9, 1.95, 0.98)

In total 475+(250×7)=2.3 ml:0.023 g of BSA added to 2.3 ml of PBS-T.

11. Add 100 µl aliquots of the allergen sample to the plate along with the standard allergen samples for the reference curve in duplicate. The standards usually go in the first two columns on the left hand side, with the least concentrated on top. Incubate for 1 hour.
12. Follow stages 5 to 6, completing a total of 5 washes.
13. Pour 11 ml of 1% BSA-PBS-T(0.11 g of BSA to 11 ml of PBS-T) to the dispensing tray. Add 11 µl of the biotinylated monoclonal antibody (refrigerator) and mix thoroughly.
14. Pipette 100 µl into each well and incubate for 1 hour at room temperature.
15. Empty plate and wash as described in stage 12. (5 washes).
16. Add 11 µl of Streptavidin (freezer) to 11 ml of 1%BSA-PBS-T. Pipette 100 µl into each well and incubate for 30 minutes. Reserve any remaining solution in a vial.
17. Empty plate and wash as described in stage 12 (5 washes).
18. Make a solution of OPD, by putting the two tablets (in silver and gold foil) into 20 ml of distilled water (in a glass vial). Shake quite vigorously in the dark until the tablets have dissolved (wrap the vial up either in tin foil or paper towel).
19. Add a small amount to the remaining solution from stage 16. Wait for a colour change (positive reaction). Add 200 µl to each well and incubate for a minimum of 30 minutes in the dark.
20. Read the plate at 450 nm/405 nm if filter not available.

Examples 1 to 26

The deactivants, as set out in the following table, were used against Der-f allergens according to the above procedure and the results are as given below. Tannic acid was used as a comparator. What was measured after treatment with deactivant and tannic acid was the amount of allergen remaining active after treatment. The ratio of amount of remaining active allergen after treatment with deactivant and tannic acid is also given.

TABLE

| Example | Deactivant | Amount of Allergen remaining active after deactivant treatment | Amount of Allergen remaining active after tannic acid treatment | Ratio of remaining active allergen after Deactivant/Tannic Acid Treatment | Number |
|---|---|---|---|---|---|
| 1 | Urea | 3750 | 1500 | 2.500 | xxi |
| 2 | Polymeric dialdehyde | 1325 | 550 | 2.409 | xx |
| 3 | Cedarwood oil | 1800 | 750 | 2.400 | i |
| 4 | Cyclodextrin | 3850 | 1700 | 2.265 | xxii |
| 5 | hexadecyltrimethylammonium chloride | 4075 | 1800 | 2.264 | ii |
| 6 | Aluminium chlorohydrate | 1675 | 750 | 2.233 | iii |
| 7 | 1-propoxy-propanol-2 | 3950 | 1800 | 2.194 | iv |
| 8 | Silica Gel (Kent) | 2037.5 | 933.5 | 2.183 | vi |
| 9 | polyquaternium-10 (Polymer JR-125) | 4335 | 2000 | 2.168 | v |
| 10 | Hydrogenated Hop Oil | 1100 | 550 | 2.000 | xxiii |
| 11 | Propylene glycol alginate | 3175 | 1700 | 1.868 | vii |
| 12 | Poly vinyl pyrrolidone | 2450 | 1425 | 1.719 | xxiv |
| 13 | Ammonium sulphate | 2750 | 1700 | 1.618 | viii |
| 14 | Hinokitol (0.5%) | 3065 | 2000 | 1.533 | ix |
| 15 | N-methyl pyrrolidone | 1600 | 1175 | 1.362 | xxv |
| 16 | L-Ascorbic Acid | 2000 | 1500 | 1.333 | x |
| 17 | Immobilised Tannic Acid | 1550 | 1175 | 1.319 | xi |
| 18 | Aerosol OT | 1525 | 1175 | 1.298 | xviii |
| 19 | Chlorohexidine | 1412.5 | 1425 | 0.991 | xii |
| 20 | Parsley Camphor | 1225 | 1387.5 | 0.883 | xix |
| 21 | Maleic anhydride | 1312.5 | 1500 | 0.875 | xiii |
| 22 | Anthraquinone sodium salt | 1530 | 2000 | 0.765 | xxvi |
| 23 | Hinoki oil | 1025 | 1387.5 | 0.739 | xiv |
| 24 | Composite of AgCl and $TiO_3$ | 1025 | 1425 | 0.719 | xv |
| 25 | Germall II | 950 | 1387.5 | 0.685 | xvi |
| 26 | Thymol | 725 | 1387.5 | 0.523 | xvii |

Examples 27 to 47

The deactivants, as set out in the following table, were used against Der-f allergens according to the above procedure and the results are as given below. What was measured were the amount of allergens remaining after treatment with deactivant and the amount of allergens remaining after vacuuming with no deactivant treatment.

TABLE

| Example | Deactivant | Amount of active Allergen remaining after deactivant treatment | Amount of active Allergen remaining after no deactivant treatment but only vaccuming | Deactivant |
|---|---|---|---|---|
| 1 | Glutaraldehyde | 816 | 3375 | xxviii |
| 2 | Polymeric dialdehyde | 2792 | 3375 | xx |
| 3 | Cedarwood oil | 3375 | 6000 | i |
| 4 | hexadecyltrimethylammonium chloride | 2863 | 4992 | ii |
| 5 | Aluminium chlorohydrate | 978 | 4992 | iii |
| 6 | 1-propoxy-propanol-2 | 1233 | 4992 | iv |
| 7 | Silica Gel (Kent) | 1540 | 4992 | vi |
| 8 | polyquaternium-10 (Polymer JR-125) | 5463 | 6250 | v |
| 9 | Propylene glycol alginate | 3781 | 6250 | vii |
| 10 | Ammonium sulphate | 2325 | 6250 | viii |
| 11 | Potassium thioglycolate | 3092 | 3375 | xxvii |
| 12 | Hinokitol (0.5%) | 2058 | 3375 | ix |
| 13 | L-Ascorbic Acid | 1438 | 5642 | x |
| 14 | Immobilised Tannic Acid | 1125 | 5642 | xi |
| 15 | Aerosol OT | 4494 | 5642 | xviii |
| 16 | Chlorohexidine | 2281 | 4450 | xii |
| 17 | Parsley Camphor | 2581 | 4450 | xix |
| 18 | Maleic anhydride | 783 | 4450 | xiii |
| 19 | Hinoki oil | 1644 | 3400 | xiv |
| 20 | Composite of AgCl and $TiO_2$ | 1632 | 3400 | xv |
| 21 | Thymol | 1500 | 3400 | xvii |

Example 48–55

Further samples were tested as above and compared tannic acid. The ratio of actives remaining deactivant treatment and actives remaining after acid treatment are given below:

| Example | Deactivant | Ratio of actives remaining after deactivant treatment over those remaining after tannic acid treatment | Number |
|---|---|---|---|
| 48 | Germall II | 1.5 | vi |
| 49 | N-methyl pyrrolidone | 4.0 | xv |
| 50 | Hinoki Oil | 4.0 | iv |
| 51 | Silver chloride/$TiO_2$ | 3.5 | v |
| 52 | Thymol | 4.0 | vii |
| 53 | Chlorohexidine | 3.0 | ii |
| 54 | Maleic anhydride | 1.0 | iii |
| 55 | Glutaraldehyde | 1.5 | xviii |

Examples 56–59

The following formulations can be made up as carrier compositions for use in an aerosol for deactivating Der-f and Der-p allergens.

Example 56

| Raw Ingredient Description By Weight | Item Classification | % |
|---|---|---|
| Anhydrous Ethanol (SD Alcohol 40) | Solvent | 79.646 |
| Alkyl dimethyl benzyl ammonium saccharinate | Cationic Surfactant | 0.106 |
| Corrosion Inhibitor (I) | | 0.192 |
| Corrosion Inhibitor (II) | | 0.192 |
| Corrosion Inhibitor (III) | | 0.096 |
| Deionized Water | Water/Solvent | 15.768 |
| Carbon Dioxide | Propellant | 4.000 |
| TOTAL | | 100.000 |

Example 57

| Raw Ingredient Description by Weight | Item Classification | % |
|---|---|---|
| Anhydrous Ethanol (SD Alcohol 40) | Solvent | *57.000 |
| Fragrance#17 | Fragrance | 0.0500 |
| Dow Corning 193 Surfactant | Surfactant | 0.025 |
| Corrosion Inhibitor (I) | | 0.100 |
| Corrosion Inhibitor (II) | | 0.100 |
| Deionized Water | Water/solvent | *14.725 |
| NP-40/Butane 40 | Hydrocarbon propellant | 28.000 |
| TOTAL | | 100.000 |

*= May replace with 95% Ethanol (SD Alcohol 40) at 61.755% by weight and 9.970% by weight Deionized water

Example 58

| Raw Ingredient Description by Weight | Item Classification | % |
|---|---|---|
| Anhydrous Ethanol (SD Alcohol 40) | Solvent | 79.646 |

-continued

| Raw Ingredient Description by Weight | Item Classification | % |
|---|---|---|
| Benzyl Benzoate-an acaricide | Active/ester | 4.600 |
| Alkyl dimethyl benzyl ammonium saccharinate | Cationic Surfactant | 0.106 |
| Corrosion Inhibitor (I) | | 0.192 |
| Corrosion Inhibitor (II) | | 0.192 |
| Corrosion Inhibitor (III) | | 0.096 |
| Deionized Water | Water/solvent | 11.168 |
| Carbon Dioxide | Propellant | 4.000 |
| TOTAL | | 100.000 |

Example 59

| Raw Ingredients Description by weight | Item Classification | % |
|---|---|---|
| Anhydrous Ethanol (SD Alcohol 40) | Solvent | *57.000 |
| Benzyl Benzoate | Active/ester | 4.600 |
| Fragrance#17 | Fragrance | 0.0500 |
| Dow Corning 193 Surfactant | Surfactant | 0.025 |
| Corrosion Inhibitor (I) | | 0.100 |
| Corrosion Inhibitor (II) | | 0.100 |
| Deionized Water | Water/solvent | *10.125 |
| NP-40/Butane 40 | Hydrocarbon propellant | 28.000 |
| TOTAL | | 100.000 |

*= May replace 95% Ethanol (SD Alcohol 40) at 61.755% by weight and 5.370% by weight Deionized water.

What is claimed is:

1. A method for deactivating a Der-f and/or Der-p allergen present on a textile surface comprising contacting the allergen with a deactivating effective amount of one or more of deactivants selected from i) cedarwood oil,
ii) hexadecyltrimethylammonium chloride,
iii) aluminium chlorohydrate,
iv) 1-propoxy-propanol-2,
v) polyquaternium-10
vi) silica gel,
vii) propylene glycol alginate,
viii) ammonium sulphate,
ix) hinokitiol
x) L-ascorbic acid,
xi) immobilised tannic acid,
xii) chlorohexidine,
xiii) maleic anhydride
xiv) hinoki oil,
xv) a composite of AgCl and TiO$_2$,
xvi) diazolidinyl urea,
xvii) a compound of formula I

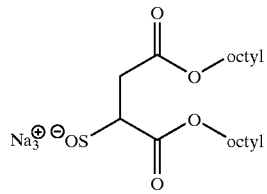

xviii) the compound of formula II

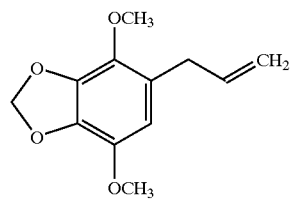

xix) a polymeric dialdehyde containing two or more of a recurring unit of the formula III

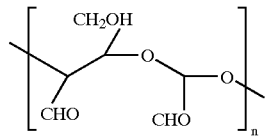

where n=2 to 200,
xx) urea,
xxi) cyclodextrin
xxii) hydrogenated hop oil,
xxiii) polyvinylpyrrolidone,
xxiv) N-methylpyrrolidone,
xxv) the sodium salt of anthraquinone, and
xxvi) potassium thioglycolate.

2. A method according to claim 1, in which the deactivant is selected from
xiv) hinoki oil,
xv) a composite of AgCl and TiO$_2$,
xvi) diazolidinyl urea,
xii) chlorohexidine,
xiii) maleic anhydride,
xxv) the sodium salt of anthraquinone,
xxvii) a compound of formula I, and
xviii) the compound of formula II.

3. A method according to claim 2 in which the deactivant is (xvi) diazolidinyl urea.

4. A method according to claim 2 in which the deactivant is (xvii) a compound of formula I.

5. A method according to claim 1 in which the deactivant is (xi) immobilised tannic acid.

6. A method for deactivating a Der-f allergen present on a textile surface comprising contacting the allergen with a deactivating effective amount of one or more deactivants selected from
i) cedarwood oil,
ii) hexadecyltrimethylammonium chloride,
iii) aluminium chlorohydrate,
iv) 1-propoxy-propanol-2, v) polyquaternium-10
vi) silica gel,
vii) propylene glycol alginate,
viii) ammonium sulphate
ix) hinokitiol,
x) L-ascorbic acid,
xi) immobilised tannic acid,
xii) chlorohexidine,
xiii) maleic anhydride
xiv) hinoki oil,
xv) a composite of AgCl and TiO$_2$,
xvi) diazolidinyl urea,
xvii) a compound of formula I

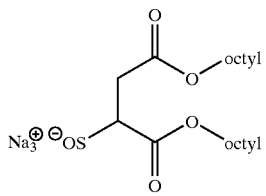

xviii) the compound of formula II

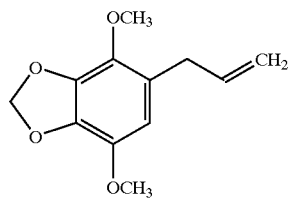

xix) a polymeric dialdehyde containing two or more of a recurring unit of the formula III

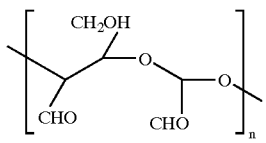

where n=2 to 200,
xx) urea,
xxi) cyclodextrin
xxii) hydrogenated hop oil,
xxiii) polyvinylpyrrolidone,
xxiv) N-methylpyrrolidone, and
xxv) the sodium salt of anthraquinone.

7. A method for deactivating a Der-p allergen present on a textile surface comprising contacting the allergen with a deactivating effective amount of one or more deactivants selected from
i) cedarwood oil,
ii) hexadecyltrimethylammonium chloride,
iii) aluminium chlorohydrate,
iv) 1-propoxy-propanol-2,
v) polyquaternium-10
vi) silica gel,
vii) propylene glycol alginate,
viii) ammonium sulphate
ix) hinokitiol,
x) L-ascorbic acid,
xi) immobilised tannic acid,
xii) chlorohexidine,
xiii) maleic anhydride
xiv) hinoki oil,
xv) a composite of AgCl and TiO$_2$,
xvi) diazolidinyl urea,
xvii) a compound of formula I

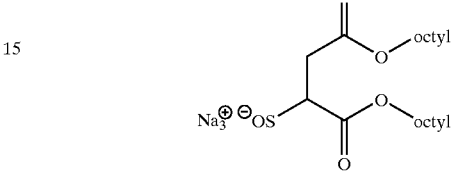

xviii) the compound of formula II

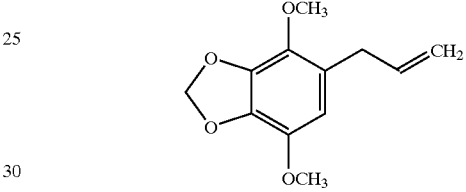

xix) a polymeric dialdehyde containing two or more of a recurring unit of the formula III

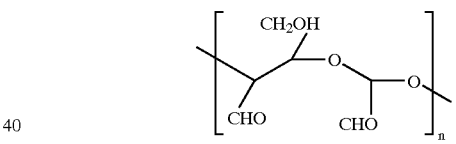

where n=2 to 200, and
xx) potassium thioglycolate.

8. A method for deactivating allergens deriving from Der-f and/or Der-p dust mites, said allergens being associated with fecal particles excreted by said mites on the surfaces of fabric materials selected from rugs and upholstered furniture, which method comprises applying to said fabric materials a deactivant selected from
i) cedarwood oil,
ii) hexadecyltrimethylammonium chloride,
iii) aluminium chlorohydrate,
iv) 1-propoxy-propanol-2,
v) polyquaternium-10
vi) silica gel,
vii) propylene glycol alginate,
viii) ammonium sulphate
ix) hinokitiol,
x) L-ascorbic acid,
xi) immobilised tannic acid,
xii) chlorohexidine,
xiii) maleic anhydride
xiv) hinoki oil, xv) a composite of AgCl and TiO$_2$,
xvi) diazolidinyl urea,
xvii) a compound of formula I

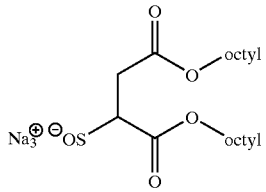

xviii) the compound of formula II

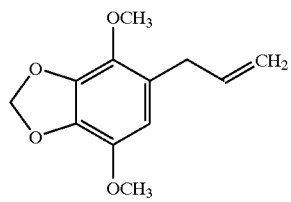

xix) a polymeric dialdehyde containing two or more of a recurring unit of the formula III

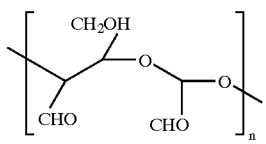

where n=2 to 200,
xx) urea,
xxi) cyclodextrin,
xxii) hydrogenated hop oil,
xxiii) polyvinylpyrrolidone,
xxiv) N-methylpyrrolidone,
xxv) the sodium salt of anthraquinone, and
xxvi) potassium thioglycolate,
at an application rate of from 16 grams to 170 grams of deactivant per 10 square meters.

9. A method according to claim 8 which the allergens derive from Der-f dust mites and the deactivant is selected from
i) cedarwood oil,
ii) hexadecyltrimethylammonium chloride,
iii) aluminium chlorohydrate,
iv) 1-propoxy-propanol-2,
v) polyquaternium-10
vi) silica gel,
vii) propylene glycol alginate,
viii) ammonium sulphate
ix) hinokitiol,
x) L-ascorbic acid,
xi) immobilised tannic acid,
xii) chlorohexidine,
xiii) maleic anhydride
xiv) hinoki oil,
xv) a composite of AgCl and TiO$_2$, xvi) diazolidinyl urea,
xvii) a compound of formula I

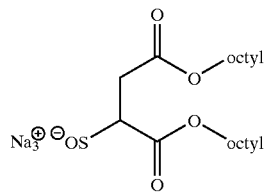

xix) the compound of formula II

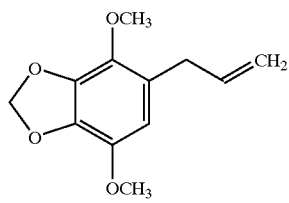

xix) a polymeric dialdehyde containing two or more of a recurring unit of the formula III

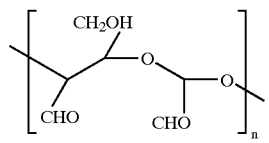

where n=2 to 200,
xx) urea,
xxi) cyclodextrin,
xxii) hydrogenated hop oil,
xxiii) polyvinylpyrrolidone,
xxiv) N-methylpyrrolidone, and
xxv) the sodium salt of anthraquinone.

10. A method according to claim 8 in which the allergens derive from Der-p dust mites and the deactivant is selected from
i) cedarwood oil,
ii) hexadecyltrimethylammonium chloride,
iii) aluminium chlorohydrate,
iv) 1-propoxy-propanol-2,
v) polyquaternium-10
vi) silica gel,
vii) propylene glycol alginate,
viii) ammonium sulphate
ix) hinokitiol,
x) L-ascorbic acid,
xi) immobilised tannic acid,
xii) chlorohexidine,
xiii) maleic anhydride
xiv) hinoki oil,
xv) a composite of AgCl and TiO$_2$, xvi) diazolidinyl urea,
xvii) a compound of formula I

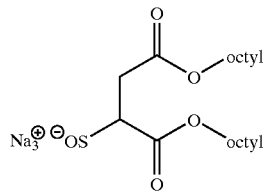

xviii) the compound of formula II

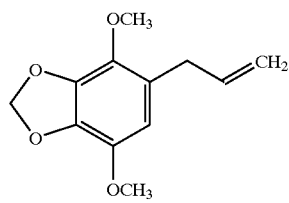

xix) a polymeric dialdehyde containing two or more of a recurring unit of the formula III

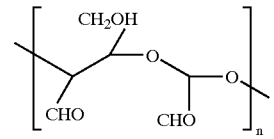

where n=2 to 200, and xx) potassium thioglycolate.

11. A method for deactivating a Der-f and/or Der-p allergen present on a textile surface containing the allergen comprising contacting the allergen with a deactivant composition in which the deactivant is 6-isopropyl-m-cresol present in an amount of from 0.01 to 3% of said composition.

* * * * *